United States Patent [19]
Morita et al.

[11] Patent Number: 5,905,033
[45] Date of Patent: May 18, 1999

[54] PROCESS FOR OBTAINING A MICROBIAL CULTURE MEDIUM FROM THE ENTRAILS OF FISH, SHELLFISH OR CEPHALOPODS AND CULTURING MICROORGANISMS USING SAME

[75] Inventors: Mikio Morita; Shigenobu Tanaka; Yuji Yokota; Isao Yumoto; Tetsuro Kusakabe, all of Sapporo, Japan

[73] Assignee: Agency of Industrial Science and Technology, Japan

[21] Appl. No.: 09/041,644

[22] Filed: Mar. 13, 1998

[30] Foreign Application Priority Data

Aug. 19, 1997 [JP] Japan ..................... 9-222423

[51] Int. Cl.$^6$ .............. C12N 1/00; C12N 1/12; C12N 1/20
[52] U.S. Cl. ............ 435/243; 435/252.1; 435/252.9; 435/253.6
[58] Field of Search ............... 435/243, 404, 435/581, 391, 408, 252.1, 252.9, 195, 29, 139, 253.6; 530/855, 857, 854, 853; 426/61, 56, 441, 602, 643, 437, 92, 59

[56] References Cited

U.S. PATENT DOCUMENTS

| | | | |
|---|---|---|---|
| 4,587,127 | 5/1986 | Akao et al. .................... | 426/46 |
| 4,820,529 | 4/1989 | Uchida et al. ................. | 426/7 |
| 4,963,370 | 10/1990 | Uchida et al. ................ | 426/7 |

FOREIGN PATENT DOCUMENTS

| | | |
|---|---|---|
| 59-071670 | 4/1984 | Japan . |
| 62-257383 | 11/1987 | Japan . |
| 63-091076 | 4/1988 | Japan . |

OTHER PUBLICATIONS

M Frobisher. The Streptococcaceae. In: Fundamentals of Microbiology, 8th Edition, pp. 420–429, 1968.

EB Lee et al. Nongop Kisul Yongu Pogo—Chungnam Taehakkyo, (Korean), 11: 120–132, 1984.

H Itoh et al. Rep. Natl. Food Res. Inst. 0(47): 31–40, 1985.

*Primary Examiner*—James C. Housel
*Assistant Examiner*—S. Devi
*Attorney, Agent, or Firm*—Lorusso & Loud

[57] ABSTRACT

A method of preparing a culture medium, including the steps of milling entrails of an aquatic product selected from fishes, shells and cephalopods; diluting the milled product with water; and hydrolyzing the diluted product. The culture medium is used for proliferating microorganisms.

11 Claims, 1 Drawing Sheet

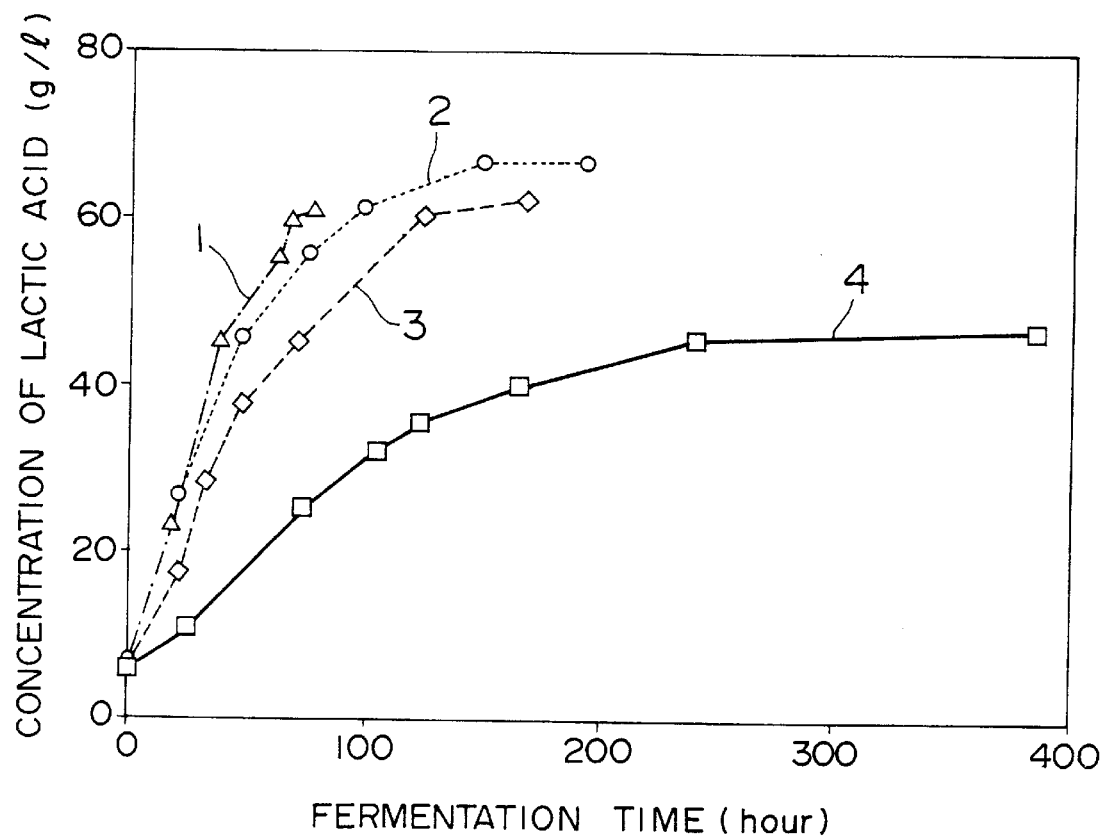

PROCESS FOR OBTAINING A MICROBIAL CULTURE MEDIUM FROM THE ENTRAILS OF FISH, SHELLFISH OR CEPHALOPODS AND CULTURING MICROORGANISMS USING SAME

This application claims the benefit of an earlier filed application, 9-222423, filed Aug. 19, 1997 in Japan.

BACKGROUND OF THE INVENTION

This invention relates to a method of preparing a culture medium from entrails of fish, shellfish or cephalopods and to a culture medium obtained thereby. The present invention is also directed to a process of growing a microorganism using the culture medium.

Nutrients such as inorganic salts, vitamins and proteins are needed for the proliferation of microorganisms. Thus, yeast extracts and peptone are generally incorporated into a culture medium. In a large scale proliferation method such as lactic fermentation, however, the use of such known nutrients which are not inexpensive brings about a problem of costs.

SUMMARY OF THE INVENTION

It is, therefore, a prime object of the present invention to provide a novel, inexpensive culture medium useful for growing microorganisms.

Another object of the present invention is to provide a method for preparing a culture medium from entrails of fish, shellfish or cephalopods.

It is a further object of the present invention to provide a process for growing a microorganism using the above culture medium.

It is yet a further object of the present invention to provide an effective utilization of garbage from fisheries.

In accomplishing the foregoing objects, the present invention provides a method of preparing a culture medium, comprising the steps of:

milling entrails of an aquatic product selected from the group consisting of fish, shellfish and cephalopods;

diluting the milled product with water; and hydrolyzing the diluted product.

The present invention also provides a culture medium obtained by the above method.

The present invention also provides a process of growing a microorganism using the above culture medium.

BRIEF DESCRIPTION OF THE DRAWING

Other objects, features and advantages of the present invention will become apparent from the detailed description of the preferred embodiments of the invention which follows, when considered in light of the accompanying drawing, in which:

the sole FIGURE consists of graphs showing the lactic acid fermentation efficiencies of various culture media.

DETAILED DESCRIPTION OF THE PREFERRED EMBODIMENTS OF THE INVENTION

The culture medium according to the present invention is obtained from entrails of an aquatic product selected from fish, shellfish and cephalopods. Examples of fish include salmon, sardine and saury. Examples of shellfish include scallops. Examples of cephalopods include squid.

The entrails are washed with water and milled with a mixer, a homogenizer or any other suitable means to obtain a slurry. The slurry is diluted with water. The amount of the water is generally in the range of 3–20 times, preferably 5–13 times, the volume of the slurry.

The diluted slurry is then hydrolyzed to obtain a culture medium according to the present invention. The hydrolysis may be performed in the presence of an alkali, an acid or a hydrolase.

In the case of acid or alkali-catalyzed hydrolysis, the diluted slurry is mixed with an acid or alkali so that the pH of the slurry is adjusted to below about 4 or above about 10. The acid may be a mineral acid such as hydrochloric acid, sulfuric acid or phosphoric acid or an organic acid such as acetic acid or lactic acid. The pH-adjusted slurry is then heated, preferably at 100–150° C. in a pressure-resistant vessel, to hydrolyze and solubilize proteins, sugars, etc. and to extract vitamins, inorganic salts, etc. contained in the milled entrails. The hydrolysis time is generally 10 minutes to 10 hours. The hydrolyzed mixture is then cooled to room temperature and neutralized to a pH of about 7.

In the case of hydrolysis using a hydrolase, the diluted slurry is sterilized by heating, for example at a temperature of 100–150° C. for 1–20 minutes, and then cooled to 20–50° C. The sterilized and cooled slurry is mixed with a hydrolase and the mixture is allowed to stand at 20–50° C. for 1–3 days. Examples of the hydrolase include protease and glycosidase. Microorganisms such as yeast containing protease may also be used for the hydrolysis of the diluted slurry.

The hydrolyzed product may be used as a culture medium as such. If desired, the hydrolyzed product is separated into a liquid phase and a solid rich phase, by filtration or centrifuge, and the liquid phase is used as a culture medium according to the present invention. The liquid phase may be dried by, for example, spray drying or freeze drying to obtain a dry powder. The dry powder may be used as a culture medium after dissolution in water.

Cultivation of a microorganism using the culture medium according to the present invention may be carried out in a conventional manner producing a metabolic or fermentation product such as an amino acid or an organic acid. Depending upon the purpose of the cultivation, a suitable substrate (carbon source) is selected and used in a suitable amount.

The following examples will further illustrate the present invention. Percentages are by weight. In each of Examples and Comparative Examples, a preculture of *Lactobacillus amylophilus* JCM1125 (NRR1 B-4436 (DSM 20534)) was used for the production of lactic acid by fermentation. The preculture was obtained as follows:

A culture medium composed of 20 g of glucose, 10 g of polypeptone, 5 g of yeast extract, 1 g of Tween 80 (surfactant), 2 g of $K_2HPO_4$, 5 g of sodium acetate, 2 g of ammonium citrate, 0.2 g of $MgSO_4 \cdot 7\ H_2O$, 0.05 g of $MnSO_4 \cdot xH_2O$ and 1.0 liter of distilled water was heated at 120° C. for 15 minutes for the sterilization thereof and then cooled to room temperature. *Lactobacillus amylophilus* JCM1125 was inoculated in the culture medium and cultured therein at 30° C. for 3 days to obtain the preculture.

EXAMPLE 1

500 Grams of entrails of squids (water content: about 85%) and 4,200 g of potato (starch content: about 14%) were milled with a mixer to obtain a slurry. This was placed in a 20 liter fermentation jar together with 4 liters of water, 50 g of lactic acid and 3.5 g of phosphoric acid so that the resulting mixture had a pH of 3.2. The mixture was then heated at about 130° C. for 1 hour to solubilize the potato and squid entrails and to sterilize the mixture (about 25% of the proteins in the squid entrails were solubilized). After being cooled to 30° C., the resulting mixture was inoculated with 0.4 liter of the *Lactobacillus amylophilus* JCM1125 preculture and 7.5 g of Tween 80 was then added. The mixture was then allowed to stand at 30° C. while maintaining the pH thereof at 6.5 with aqueous ammonia. The cumulative amount of L-lactic acid produced by fermentation was measured. The results are shown in the FIGURE as curve 1.

EXAMPLE 2

1,600 Grams of entrails of scallops (water content: about 85%) and 6,650 g of potato (starch content: about 20%) were milled with a mixer to obtain a slurry. This was placed in a 20 liter fermentation jar together with 11.4 liters of water, 50 g of lactic acid and 4.2 g of phosphoric acid so that the resulting mixture had a pH of 3.5. The mixture was then heated at about 130° C. for 1 hour to solubilize the potato and scallop entrails and to sterilize the mixture (about 35% of the proteins of the scallop entrails was solubilized). After being cooled to 30° C., the resulting mixture inoculated was inoculated with 2 liters of the *Lactobacillus amylophilus* JCM1125 preculture. 15 g of Tween 80, 7.5 g of sodium acetate, 7.5 g of ammonium citrate, 3 g of $MgSO_4 \cdot 7\ H_2O$ and 0.75 g of $MnSO_4 \cdot xH_2O$ were then added to the mixture and it was allowed to stand at 30° C., while maintaining the pH thereof at 6.5 with aqueous ammonia. The cumulative amount of L-lactic acid produced by fermentation was measured. The results are shown in the FIGURE as curve 2.

Comparative Example 1

6,730 g of potato (starch content: about 20%) were milled with a mixer to obtain a slurry. This was placed in a 20 liter fermentation jar together with 11.4 liters of water, 50 g of lactic acid and 4.2 g of phosphoric acid so that the resulting mixture had a pH of 3.5. The mixture was then heated at about 130° C. for 1 hour to solubilize the potato and to sterilize the mixture. After being cooled to 30° C., the resulting mixture was inoculated with 2 liters of the *Lactobacillus amylophilus* JCM1125 preculture and 15 g of Tween 80, 150 g of polypeptone, 75 g of yeast extract, 2.41 g of KOH, 7.5 g of sodium acetate, 7.5 g of ammonium citrate, 3 g of $MgSO_4 \cdot 7\ H_2O$ and 0.75 g of $MnSO_4 \cdot xH_2O$ and allowed to stand at 30° C. while maintaining the pH thereof at 6.5 with aqueous ammonia. The cumulative amount of L-lactic acid produced by fermentation was measured. The results are shown in the FIGURE as curve 3.

Comparative Example 2

6,760 g of potato (starch content: about 20%) were milled with a mixer to obtain a slurry. This was placed in a 20 liter fermentation jar together with 11.4 liters of water, 50 g of lactic acid and 4.2 g of phosphoric acid so that the resulting mixture had a pH of 3.3. The mixture was then heated at about 130° C. for 1 hour to solubilize the potato and to sterilize the mixture. After being cooled to 30° C., the resulting mixture was inoculated with 2 liters of the *Lactobacillus amylophilus* JCM1125 preculture and 15 g of Tween 80, 2.41 g of KOH, 7.5 g of sodium acetate, 7.5 g of ammonium citrate, 3 g of $MgSO_4 \cdot 7\ H_2O$ and 0.75 g of $MnSO_4 \cdot xH_2O$ were added and it was allowed to stand at 30° C. while maintaining the pH thereof at 6.5 with aqueous ammonia. The cumulative amount of L-lactic acid produced by fermentation was measured. The results are shown in the FIGURE as curve 4.

The culture mediums employed in each of the above examples and comparative examples are summarized in Table below. Except for the amounts of water, preculture and total volume (liter), the units for the amounts of respective ingredients shown in Table are all g (gram).

TABLE

| | Example | | Comparative Example | |
|---|---|---|---|---|
| | 1 | 2 | 1 | 2 |
| Potato | 4,200 | 6,650 | 6,730 | 6,760 |
| (Starch) | 590 | 1,330 | 1,350 | 1,350 |
| Squid entrails | 500 | | | |
| Scallop entrails | | 1,600 | | |
| Polypeptone | | | 150 | |
| Yeast extract | | | 75 | |
| Tween 80 | 7.5 | 15 | 15 | 15 |
| $H_3PO_4$ | 3.5 | 4.2 | 4.2 | 4.2 |
| KCH | | | 2.41 | 2.41 |
| Sodium acetate | | 7.5 | 7.5 | 7.5 |
| Ammonium citrate | | 7.5 | 7.5 | 7.5 |
| $MgSO_4 \cdot 7H_2O$ | | 3 | 3 | 3 |
| $MnSO_4 \cdot xH_2O$ | | 0.75 | 0.75 | 0.75 |
| Water | 4 | 11.4 | 11.4 | 11.4 |
| Preculture | 0.4 | 2 | 2 | 2 |
| Total volume | 8.1 | 18.7 | 18.8 | 17.8 |

As will be appreciated from the results shown in the FIGURE, when only inorganic salts are contained in the culture medium (Curve 4; Comparative Example 2), the lactic acid fermentation of starch occurs at a low fermentation rate; the lactic acid concentration is only about 48 g/liter after 360 hours from the commencement of the culture and the lactic acid yield is about 63%.

When conventionally used polypeptone and yeast extract are used instead (Curve 3, Comparative Example 1), the fermentation proceeds satisfactorily; the lactic acid concentration is about 62 g/liter after 170 hours from the commencement of the fermentation and the lactic acid yield is about 87%.

When the polypeptone and yeast are replaced by treated scallop entrails (Curve 2, Example 2), the fermentation proceeds more rapidly; the lactic acid concentration is about 67 g/liter after 150 hours from the commencement of the fermentation and the lactic acid yield is about 94%.

When the polypeptone and yeast are replaced by treated squid entrails and the inorganic salts are removed (Curve 1, Example 1), the fermentation proceeds more rapidly; the lactic acid concentration is about 61 g/liter after 78 hours from the commencement of the fermentation and the lactic acid yield is about 84%.

Thus, the culture medium according to the present invention provides cultivation efficiency comparable to or higher than that attained by the use of conventional polypeptone.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method of preparing a culture medium for microorganisms, comprising the steps of:
   providing entrails separated from an aquatic product selected from the group consisting of fish, shellfish and cephalopods;

milling the separated entrails to produce a milled product;

diluting said milled product with water; and hydrolyzing the diluted product to produce the culture medium.

2. A method as claimed in claim 1, wherein said hydrolysis is performed in the presence of a hydrolase, an alkali or an acid.

3. A method as claimed in claim 1, further comprising separating said hydrolyzed product into a liquid phase and a solid-rich phase.

4. A method as claimed in claim 2, further comprising neutralizing said hydrolyzed product.

5. A method as claimed in claim 3, further comprising drying said liquid phase.

6. A method as claimed in claim 1, wherein said aquatic product is selected from the group consisting of squids, scallops, salmon, sardine and saury.

7. A culture medium obtained by a method according to claim 1.

8. A process for growing microorganisms comprising adding said microorganisms to a culture medium for proliferation of said microorganisms, said culture medium obtained by a method comprising:

providing entrails separated from an aquatic product selected from the group consisting of fish, shellfish and cephalopods;

milling the separated entrails to produce a milled product;

diluting said milled product with water; and hydrolyzing the diluted product to produce the culture medium.

9. A process as claimed in claim 8, wherein said microorganisms are lactic acid bacteria, so that L-lactic acid is produced as a result of the growth of said lactic acid bacteria.

10. A process as claimed in claim 8 wherein said microorganism are added as a preculture to said culture medium.

11. A process as claimed in claim 9 wherein said microorganism are added as a preculture to said culture medium.

* * * * *